(12) United States Patent
Schafer et al.

(10) Patent No.: US 6,684,705 B1
(45) Date of Patent: Feb. 3, 2004

(54) ROLLER MECHANISM USING AN ARRAY OF ULTRASOUND ELEMENTS TO INTERROGATE WOOD PROPERTIES

(75) Inventors: Mark E. Schafer, Ambler, PA (US); Raymond W. McIntyre, Warrington, PA (US); Michael K. Knauer, Norristown, PA (US)

(73) Assignee: U.S. Natural Resources, Inc.

( * ) Notice: Subject to any disclaimer, the term of this patent is extended or adjusted under 35 U.S.C. 154(b) by 0 days.

(21) Appl. No.: 09/522,642

(22) Filed: Mar. 10, 2000

Related U.S. Application Data
(60) Provisional application No. 60/133,015, filed on May 7, 1999.

(51) Int. Cl.[7] .................... G01N 29/00; G01N 29/04
(52) U.S. Cl. ..................... 73/618; 73/625; 73/628; 73/633; 73/641; 73/598; 73/600
(58) Field of Search ................. 73/579, 584, 587, 73/596, 597, 598, 599, 600, 602, 618, 622, 632, 635, 645, 646, 659, 625, 628, 633, 641

(56) References Cited

U.S. PATENT DOCUMENTS

| | | | |
|---|---|---|---|
| 3,332,278 A | * 7/1967 | Wood et al. | 73/628 |
| 3,664,180 A | * 5/1972 | McDonald et al. | |
| 3,776,026 A | * 12/1973 | Adler et al. | 73/67.7 |
| 5,143,072 A | * 9/1992 | Kantorovich et al. | 73/597 |
| 5,237,870 A | * 8/1993 | Fry et al. | 73/598 |
| 5,531,116 A | * 7/1996 | Chang et al. | 73/597 |
| 5,804,728 A | * 9/1998 | Beall et al. | 73/622 |
| 5,824,908 A | * 10/1998 | Schindel et al. | 73/602 |
| 6,029,522 A | * 2/2000 | Schafer et al. | 73/645 |
| 6,155,982 A | * 12/2000 | Hunt | 29/25.35 |
| 6,276,209 B1 | * 8/2001 | Schafer et al. | 73/597 |

FOREIGN PATENT DOCUMENTS

JP    61-286750    * 12/1986

OTHER PUBLICATIONS

EPO Supplementary European Search Report dated Dec. 16, 2002 (EP 00 93 2085).

Sandoz, J.L., "Ultrasonic solid wood evaluation in industrial applications," *NDTnet*, Dec. 1996, 1(12), 1–6.

Schmoldt, D.L., et al., "Ultrasonic defect detection in wooden pallet parts for quality sorting", *SPIE—Nondestructive Evaluation of Materials and Composites, vol. 2944*, 1996, 285–295.

* cited by examiner

*Primary Examiner*—Helen Kwok
(74) *Attorney, Agent, or Firm*—Woodcock Washburn LLP

(57) ABSTRACT

The present invention provides a method, system, and an apparatus for detecting anomalies in a wooden member. The apparatus includes a first roller device comprising a first array of transducers, and a second roller device comprising a second array of transducers. A first transducer in the first array of transducers communicates with more than one transducer in the second array of transducers. The apparatus may be designed such that the wooden member may pass between the first roller device and the second roller device. In addition, the first array of transducers and the second array of transducers maintain an orientation perpendicular to the moving direction of the wooden member as the first roller device and the second roller device roll along the wooden member. Each of the transducers operate in an ultrasonic frequency range. Also, each transducer in the first array of transducers is acoustically isolated from each other transducer.

17 Claims, 7 Drawing Sheets

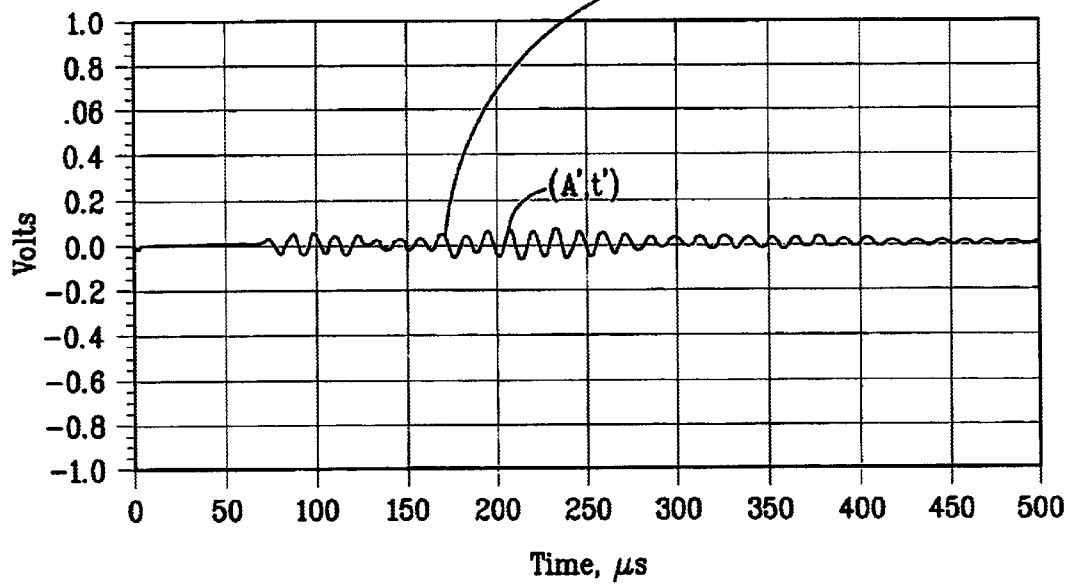
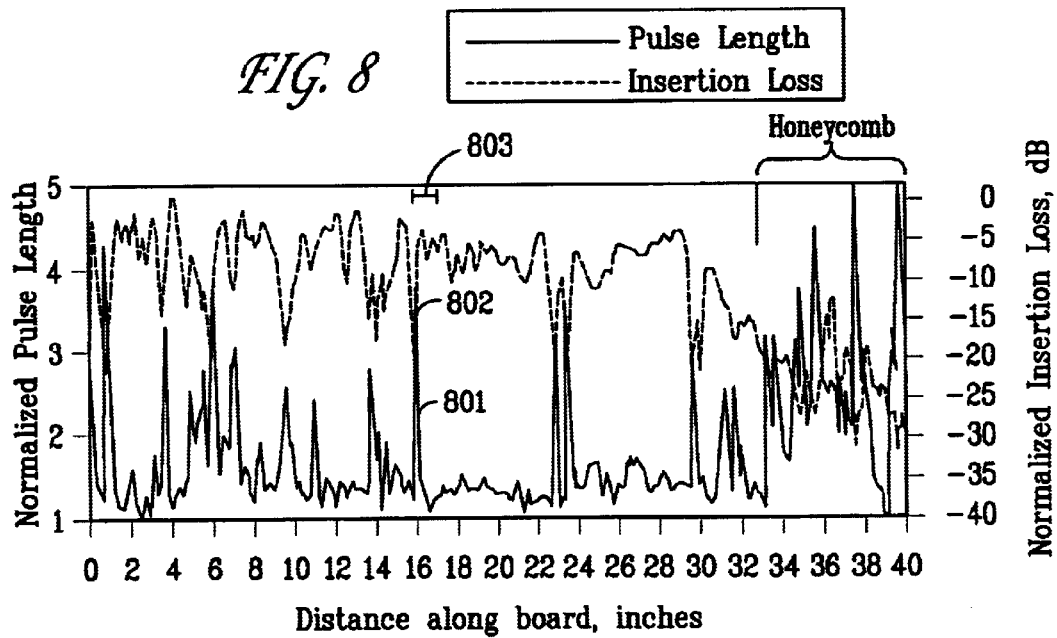

ROLLER MECHANISM USING AN ARRAY OF ULTRASOUND ELEMENTS TO INTERROGATE WOOD PROPERTIES

CROSS REFERENCE TO RELATED APPLICATIONS

This application claims priority under 35 U.S.C. §119(e) to U.S. Provisional Application No. 60/133,015, filed May 7, 1999.

FIELD OF THE INVENTION

The present invention relates to the use of ultrasound testing to detect anomalies in wooden members. More specifically, the present invention relates to the use of a roller device housing an ultrasonic transducer element array for the ultrasound testing of wooden members.

BACKGROUND OF THE INVENTION

The grading of wooden members is important to the entire lumber and construction industry. Accurate grading allows a builder to match the strength of the wooden member to the type of construction project. In addition, proper grading permits a sawmill to charge a premium for stronger members, while dedicating weaker members for more appropriate tasks. Grading techniques have been developed that nondestructively measure certain physical properties of wooden members. One such technique uses ultrasonic waves to measure physical properties.

Ultrasound measurement systems often use rolling transducers to detect anomalies in, and thus the strength of, the wooden member. By passing an ultrasonic wave of known characteristics through the wooden member, the system is able to detect anomalies by analyzing a modification of the wave after it passes through the member. Specifically, a transducer located on one side of the wooden member directs an ultrasonic wave through the member to another transducer located on the opposite side of the wooden member. When part of the ultrasonic wave passes through the anomaly, it is modified and collected by a receiving transducer. A computer connected to the receiving transducer compares the transmitted wave with the wave that was passed through the wooden member, or with some "standard" or "ideal" wave. Based on the distorted difference between the two waves, the computer displays the anomalies on a monitor. Moreover, the system may be able to determine the type of anomaly (e.g., knots, checks, or split), its location, and its effect on the strength of the wooden member.

The demanding production line requirements of today's sawmill require that multiple characteristics of the wooden member be determined simultaneously. For structural softwood lumber and hardwood pallet stock, for example, the ultrasound measurement system must determine the location and severity of a knot at the same time it searches for other anomalies, like splits or checks (i.e., internal voids). In order to map out defects, multiple transducer systems have been used to produce rough maps of defect locations. In order to expand the coverage of the wooden members in such multiple transducer systems, the multiple transducers are staggered along the direction of movement of the wooden member (z direction), as illustrated in prior art FIG. 1A. Due to mechanical mounting clearance requirements, the transducers are staggered in the z direction and not aligned along the y axis, thereby preventing any benefits from redundancy in geometry.

Those skilled in the art will appreciate that the presence of multiple transducers creates certain operational problems. Obviously, the use of multiple individual transducers increases the mechanical complexity of the ultrasound measurement system. Also, the transmitting transducers must be separated physically from each other to allow for mechanical mounting clearance. However, this required separation of the transmitting transducers and their dedication to one receiving transducer means that certain smaller anomalies, like splits, may fall between the ultrasound waves, thus foiling detection.

FIGS. 1A and 1B provide an example of such a prior art multiple-transducer ultrasound measurement device 100 for grading a wooden member 107. As will be understood from the following description, the term wooden member includes logs, cants, lumber, boards (like structural softwood lumber and hardwood pallet stock), and wood composites in various stages of processing. FIG. 1A is a perspective view of prior art multiple-transducer ultrasound measurement device 100. As shown in FIG. 1A, multiple-transducer ultrasound device 100 includes three transmitting transducers 101–103, located adjacent to each other. Multiple-transducer ultrasound device 100 also includes three receiving transducers 104–106. Although FIG. 1A shows three transmitting transducers 101–103 and three receiving transducers 104–106, it should be appreciated that multiple-transducer ultrasound device 100 may include any number of receiving and transmitting transducers. Wooden member 107 is located between transmitting transducers 101–103 and receiving transducers 104–106.

Transmitting transducers 101–103 are separated from each other by some distance d along the z-axis. Distance d provides the necessary physical separation so that transducers do not physically interfere with each other. Receiving transducers 104–106 also are separated from each other by a distance d equal to distance d for the same reason. Separating receiving transducers 104–106 by distance d, equal to d, places receiving transducers 104–106 in the same x-axis plane as transmitting transducers 101–103. Because of this, transmitting transducer 101 communicates exclusively with receiving transducer 104, transmitting transducer 102 communicates exclusively with receiving transducer 105, and transmitting transducer 103 communicates exclusively with receiving transducer 106.

FIG. 1B is a front-view of prior art multiple-transducer ultrasound measurement device 100, further detailing communication between transmitting transducers 101–103 and receiving transducers 104–106. In operation, as wooden member 107 moves along the z-axis, transmitting transducers 101–103 roll along one side of wooden member 107, and receiving transducers 104–106 roil along the opposite side. Transmitting transducers 101–103 transmit ultrasonic waves through wooden member 107 to receiving transducers 104–106. Anomalies within wooden member 107 affect the transmitted waves as they pass through wooden member 107 (as discussed further with reference to FIG. 3). By analyzing the anomaly-affected waves received by receiving transducers 104–106, as compared to the transmitted waves or a "standard" wave (as discussed further with reference to FIG. 6), multiple-transducer ultrasound device 100 is able to provide an output that characterizes the various anomalies.

As shown in FIG. 1B, each of transmitting transducers 101–103 communicate exclusively with receiving transducers 104–106, respectively. In particular, transmitting transducers 101 sends an ultrasonic wave 110 to receiving transducer 104, transmitting transducers 102 sends an ultrasonic wave 111 to receiving transducer 105, and transmitting transducers 103 sends an ultrasonic wave 112 to receiving transducer 106. Notably, each of waves 110–112 travel in the x-direction, perpendicular to transmitting transducers 101–103, receiving transducers 104–106, and wooden member 107. Because each receiving transducer 104–106 captures wave 110–112, respectively, exclusively from one transmitting transducer 101–103, respectively, portions of waves 110–112 that stray beyond their assigned receiving transducer 104–106 are ignored. As a result, small anomalies 108 and 109 that lie on the periphery of each transducer transmitter/receiver pair 101/104, 102/105, and 103/106 may go undetected.

The solution of FIGS. 1A and 1B is depicted by Fry et al. in U.S. Pat. No. 5,237,870, where Fry et al. describe multiple, independent ultrasound transducers (Fry—FIGS. 11 and 12). Each transducer collects ultrasound information from a single aspect along the wooden member. Specifically, the information is collected along a linear arrangement of measurement points on a face of the member. Similarly, the publication "Ultrasonic defect detection in wooden pallet parts for quality sorting" (Schmoldt, D. L, R. M. Nelson, and R. J. Ross 1996. In S. Doctor, C. A. Lebowitz, and G. Y. Baaklini (eds.) Nondestructive Evaluation of Materials and Composites, SPIE 2944: 285–295) describes multiple measurements taken along the face of a board in order to create an "image" of the ultrasound properties, which are then correlated to physical properties.

There are several drawbacks in the prior art. First, the use of multiple individual transducers increases the complexity of the mechanical system as more transducers are used, for example, to increase the positional resolution of the system. As evidenced from the depictions in Fry et al., as the number of scan lines across the board increases, it is necessary to increase the number of transducer mechanisms. Because the transducers must be physically separated from one another, this requires that the transducers be spaced along the length of the wooden member. This increases the length of the mechanical system, thus further complicating it and increasing the cost.

Further, the arrangements proposed in the prior art may not be sensitive to defects, such as splits, which are of very narrow extent in the direction of the scan lines. That is, these features often may be completely between the scan lines, and therefore be undetectable by the methods described. Any feature which is significantly smaller than the ultrasound beam may also be undetectable using the methods of the prior art. As an example, because splits are often very narrow, even if a split falls directly in line with a scan line, it may be missed because the ultrasound energy will travel undisturbed on either side of the split, making it undetectable.

Therefore, there is a need to provide a more thorough system for detecting anomalies in wooden members.

SUMMARY OF THE INVENTION

The present invention provides a method and system for detecting anomalies in a wooden member. The method transmits ultrasonic waves of known characteristics from a first transducer in a first array of transducers through the wooden member, and receives the ultrasonic waves with more than one of a second array of transducers. The characteristics of the ultrasonic waves may include total energy, spectral energy distribution, temporal energy distribution, phase, and/or time of flight. The method may further comprise comparing at least one characteristic of the ultrasonic waves received by the second array of transducers with at least one corresponding characteristic of the ultrasonic waves transmitted by the first transducer, in order to identify abnormalities in the wooden member. Alternatively, the method may comprise determining a standard set of measurements by transmitting the ultrasonic waves from the first transducer through an acceptable wooden member, such as clear wood, or through a plastic element. At least one of the standard set of measurements may then be compared with at least one corresponding measurement of the wooden member, in order to identify abnormalities. In either case, the method may allow the wooden member to be graded based on the identified abnormalities.

The present invention further provides an apparatus for detecting anomalies in a wooden member. The apparatus includes a first roller device comprising a first array of transducers, and a second roller device comprising a second array of transducers. A first transducer in the first array of transducers communicates with more than one transducer in the second array of transducers. The apparatus may be designed such that the wooden member may pass between the first roller device and the second roller device. In addition, the first array of transducers and the second array of transducers maintain an orientation perpendicular to the moving direction of the wooden member as the first roller device and the second roller device roll along the wooden member. Each of the transducers operate in an ultrasonic frequency range. Also, each transducer in the first array of transducers is acoustically isolated from each other transducer.

BRIEF DESCRIPTION OF THE DRAWINGS

The above-mentioned features and advantages of the invention will be appreciated from the following detailed description of the invention, in view of the figures, of which:

FIG. 7B is a graph of the voltage-signal strength over time for an ultrasonic wave passed through a wooden member containing a defect;

FIG. 8 is a graph of two sample parameters, pulse length and insertion loss, plotted against distance along the wooden member.

DETAILED DESCRIPTION OF PREFERRED EMBODIMENT

Figure 2A:
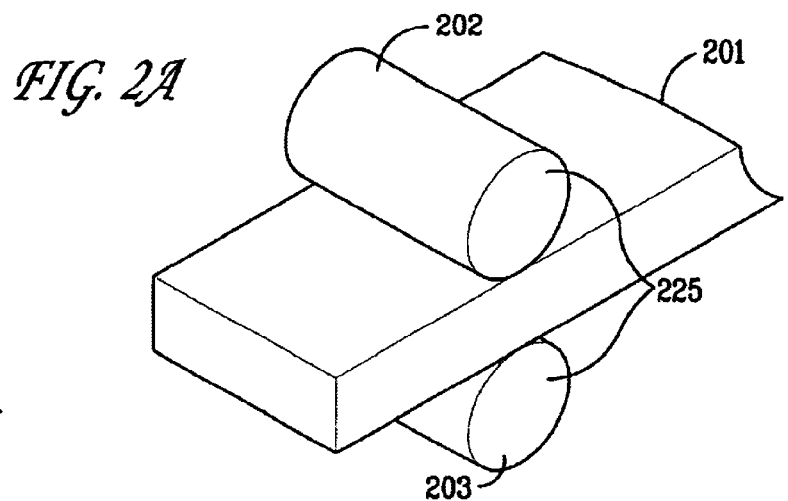
FIG. 2A is a perspective view of a roller array ultrasound measurement device, according to the present invention.
Figure 2B:
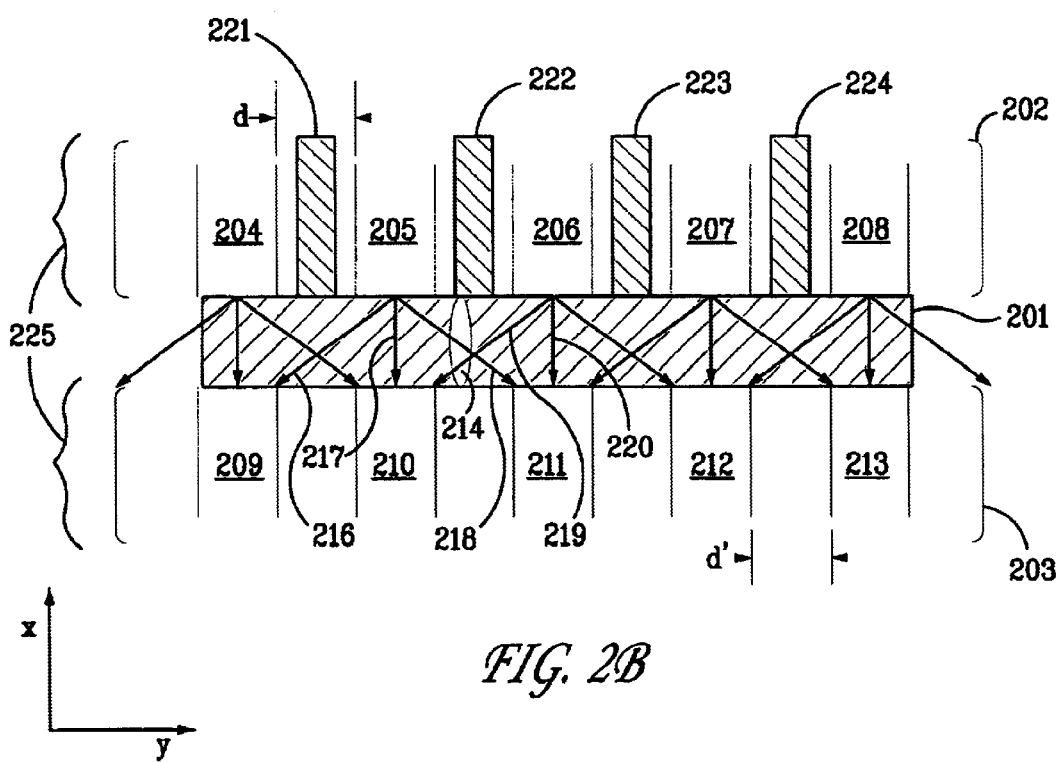
FIG. 2B is front-view of the roller array ultrasound measurement device, according to the present invention.

FIGS. 2A and 2B provide an example of a single roller ultrasound device 225 using a transducer element array 204–208 and 209–213 for grading a wooden member 107, according to the present invention. FIG. 2A is a perspective view of single roller ultrasound device 225, according to the present invention. As shown in FIG. 2A, single roller mechanism 225 includes a transmitting transducer roller device 202 and a receiving transducer roller device 203. Although discussed further with reference to FIG. 2B, it should be noted that an array of transmitting transducers 204–208 are located within transmitting transducer roller device 202, and an array of receiving transducers 208–213 are located within receiving transducer roller device 203. A wooden member 201, for example structural softwood lumber or hardwood pallet stock, is located between transmitting transducer roller device 202 and receiving transducer roller device 203.

In general, as wooden member 201 moves along the z-axis, transmitting transducer roller device 202 rolls along one side of wooden member 201, and receiving transducer roller device 203 roll along the opposite side. Transmitting transducer roller device 202 transmits ultrasonic waves through wooden member 201 to receiving transducer roller device 203. Anomalies within wooden member 201 attenuate or otherwise distort the transmitted waves as they pass through wooden member 201 (as discussed further with reference to FIG. 3). The effective apertures of transmitting transducers 204–208 and receiving transducers 209–213, as well as the sound transmission properties of wooden member 201 determine the effective ultrasonic wave through wooden member 201. By analyzing the anomaly-affected waves received by transducer roller device 203, as compared to the transmitted waves or some "standard" wave (as discussed further with reference to FIG. 3), single roller ultrasound device 225 is able to provide an output that characterizes the various anomalies.

FIG. 2B is front-view of single roller ultrasound device 225, further detailing communication between transmitting transducer roller device 202 and receiving transducer roller device 203. As shown in FIG. 2B, transmitting transducer array 204–208 is located within transmitting transducer roller device 202, and receiving transducer array 209–213 is located within receiving transducer roller device 203. Although transmitting transducer roller device 202 and receiving transducer roller device 203 are shown housing five transmitting transducers 204–208 and five receiving transducers 209–213, respectively, it should be appreciated that there may be any number of transmitting and receiving transducers. The transducers may be oriented to produce either longitudinal or shear waves through wooden member 201.

Between each of transmitting transducers 204–208 are located acoustic insulators 221–224. Acoustic insulators 221–224 ensure that the operation of one transmitting transducer 204–208 does not affect the operation of another. Transmitting transducers 204–208 are separated from each other by some distance d along the y-axis. The value of distance d is determined by the effectiveness of acoustic insulators 221–224. It should be appreciated, therefore, that distance d may be equal to the width of one acoustic insulator 221–224. FIG. 2B shows receiving transducers 209–213 also separated from each other by a distance d equal to distance d. Receiving transducers 209–213 may be located in any orientation with respect to transmitting transducers 204–208. In this way, transmitting transducers 204–208 may be arranged to communicate with any of receiving transducers 209–213.

The operation of single roller ultrasound device 225 will be described with respect to transmitting transducers 205 and 206. However, it should be appreciated that the operation of other transmitting transducers 204, 207, and 208 are consistent with this description. Each ultrasonic wave transmitted from transmitting transducers 204–208 are represented by three rays. For example, the ultrasonic wave from transmitting transducer 205 is represented by rays 216–218. Although the ultrasonic wave from each transmitting transducer 204–208 are not individual rays, such a representation furthers an understanding of the present invention. A more precise depiction of the transmitted and received ultrasonic waves will be discussed with reference to FIG. 3.

Figure 1A:
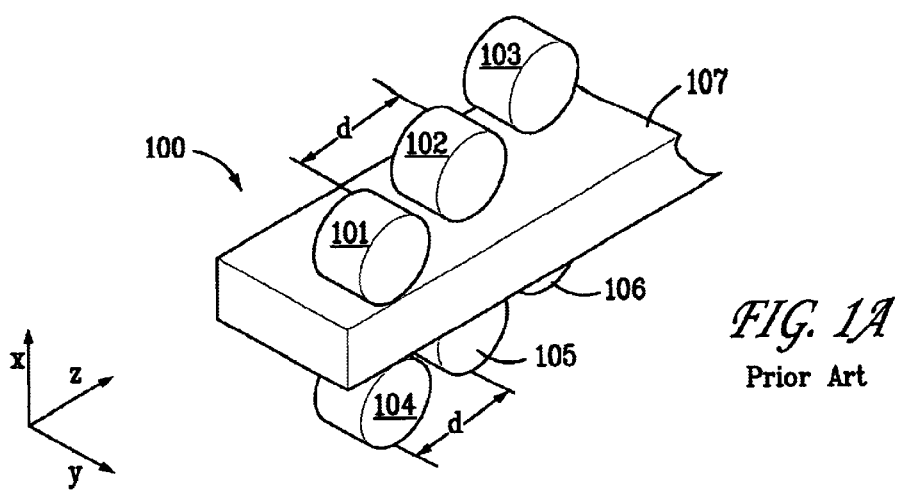
FIG. 1A is a perspective view of prior art multiple-transducer ultrasound measurement device.
Figure 1B:
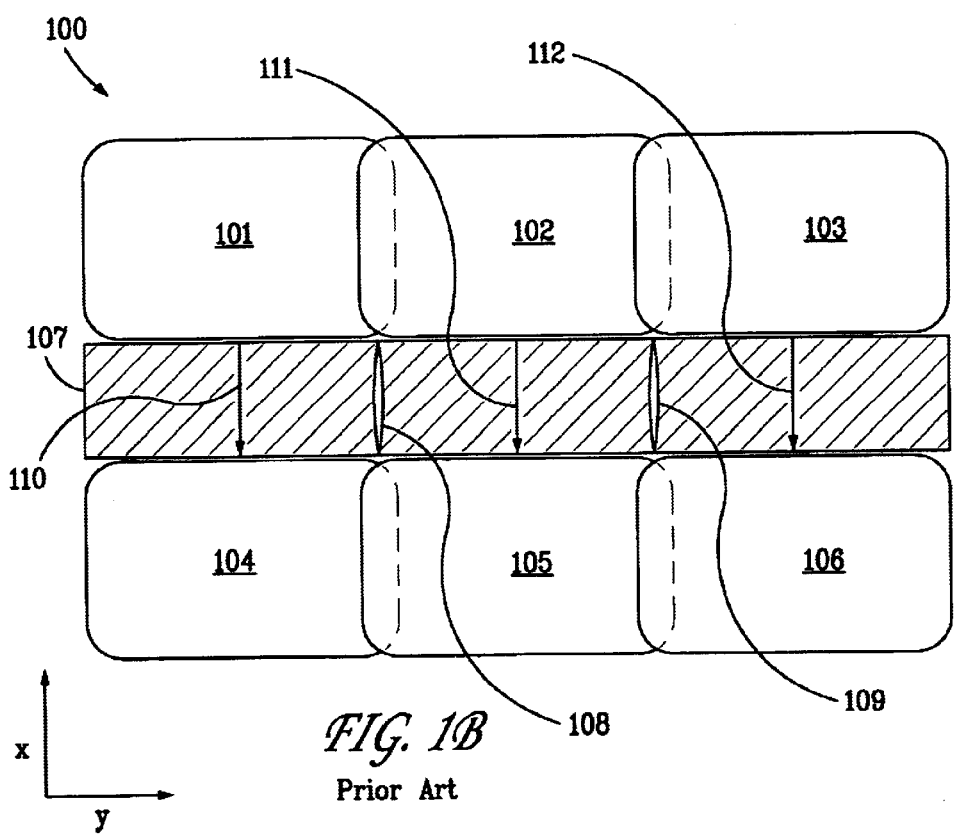
FIG. 1B is a front-view of the prior art multiple-transducer ultrasound measurement device of FIG. 1A.

As shown in FIG. 2B, all three rays 216–218 from transmitting transducer 205 are received by one of receiving transducers 209–211. Specifically, ray 216 is received by receiving transducer 209, ray 210 is received by receiving transducer 210, and ray 218 is received by receiving transducer 211. In addition, ray 219 from transmitting transducer 206 is received by receiving transducer 210, and ray 220 from transmitting transducer 206 is received by receiving transducer 211. Because ultrasound waves traveling at slant angles from transducers 204–208 are also captured and processed by receiving transducers 209–213, small anomalies do not go undetected. For example, anomaly 214 is detected by the attenuation or distortion of ray 218 from transmitting transducer 205 to receiving transducer 211. Anomaly 214 also is detected by the attenuation or distortion of ray 219 from transmitting transducer 206 to receiving transducer 210. Therefore, not only is anomaly 214 detected, but the redundant attenuation or distortion of rays 218 and 219 optimize the characterization of anomaly 214 in terms of type, extent (i.e., degree of weakening), and location. Note that this anomaly 214 would not be detected by waves 217 and 220 alone, and thus would not be detected by the ultrasonic waves 110 and 111 of prior art FIG. 1B.

Figure 3:
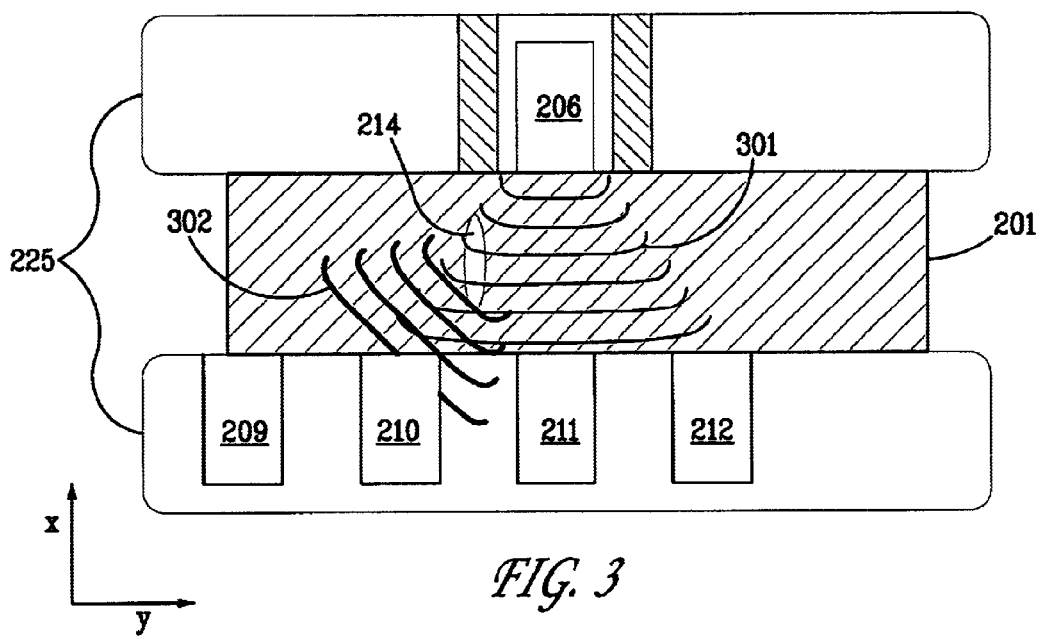
FIG. 3 is another front-view of the roller array ultrasound device, according to the present invention, showing the transmission of ultrasound waves through the wooden member.

FIG. 3 is front-view of single roller ultrasound device 225, further detailing the propagation of an ultrasonic wave 301 as it encounters anomaly 214 in wooden member 201. As shown in FIG. 3, transmitting transducer 206 transmits an ultrasonic wave 301 into wooden member 201. As ultrasonic wave 301 penetrates wooden member 201 it encounters anomaly 214. Anomaly 214 causes a portion 302 of wave 301 to be attenuated from its normal course. The attenuated portion 302 may be detected by receiving transducer 210, while the unattenuated portion of wave 301 may be detected by receiving transducers 210 and 211, for example. Therefore, by allowing wave 301 from transmitting transducer 206 to be received by receiving transducers 210 and 211, as opposed to receiving transducer 211 only, attenuated portion 302 of wave 301 is detected. Receiving attenuated portion 302 of wave 301, permits anomaly 214 to be detected by single roller ultrasound device 225. Furthermore, by extracting various parameters (as discussed with reference to FIG. 6) from transmitted wave 301 and attenuated wave 302, anomaly 214 may be further characterized in terms of type and size.

Figure 4:
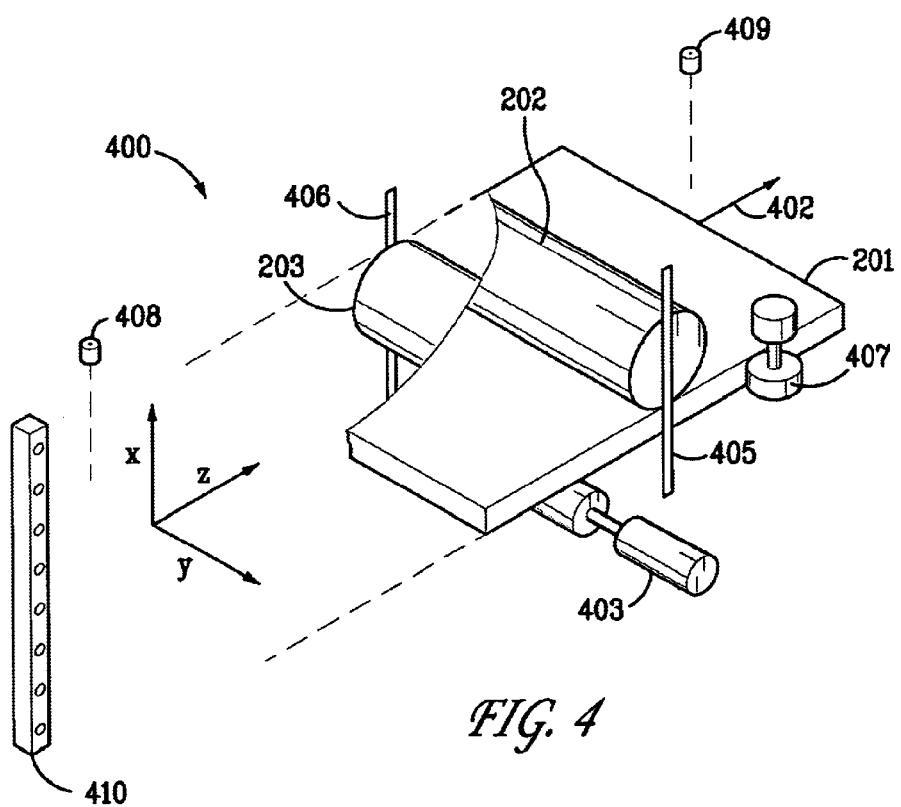
FIG. 4 is a perspective view of an ultrasound measurement system, in which the present invention may be implemented.

FIG. 4 is a perspective view of an ultrasound measurement system 400, in which the present invention may be implemented. As shown in FIG. 4, wooden member 201 is partially cutaway to reveal receiving transducer roller device 203. Wooden member 201 is shown positioned so that its grain direction and axis define the z-axis. Wooden member 201 may be moved in a translation direction 402 by one or more driving rollers 403 that support the wooden member 201 from underneath. Although wooden member is shown moving in translation direction 402, it should be appreciated that wooden member 201 may move in any direction or rotated.

Ultrasound measurement system 400 includes transmitting transducer roller device 202 and receiving transducer roller device 203. As discussed with reference to FIG. 2B, transmitting transducer roller device 202 and receiving transducer roller device 203 house individual transducers 204–213 (as shown in FIG. 2B). Transmitting transducer roller device 202 and receiving transducer roller device 203 rotate about arms 405 and 406. Therefore, transmitting transducer roller device 202 and receiving transducer roller device 203 maintain contact with the outer surface of the wooden member 201, while being free to rotate.

An encoder/roller assembly 407 positioned against the outer surface of the wooden member 201 provides a measurement of the z-axis position of wooden member 201 as it moves along the z-axis. Auxiliary sensors 408 and 409, for example photoelectric proximity sensors, may be positioned along the z-axis and directed downward along the x-axis to detect the beginning and end of the wooden member 201 as it moves, and thus provide a measurement the length of wooden member 201. A sensor array 410 having multiple photoelectric sensors (not numbered) arrayed along the x-axis may be provided in order to measure the height of wooden member 307.

Figure 5:
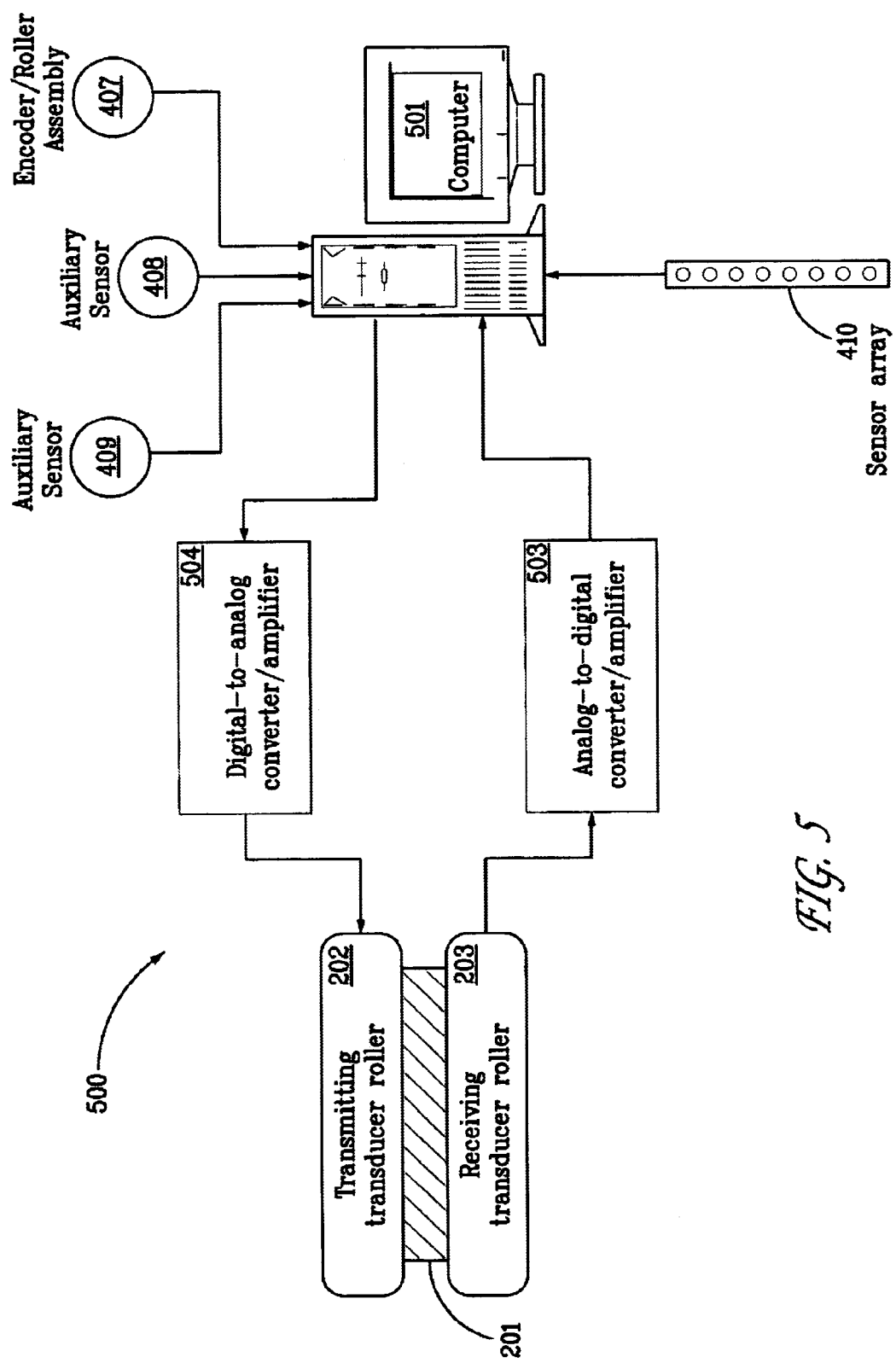
FIG. 5 is a block diagram of an ultrasound measurement system, according to the present invention.

FIG. 5 is a block diagram of ultrasound measurement system 500, according to the present invention. Ultrasound measurement system 500 includes a standard desktop computer 501, using a WINDOWS operating system and an INTEL PENTIUM processor chip set, for example. Computer 501 includes a processor (not shown), and electronic memory (not shown) of a type familiar to those of ordinary skill in the art. Computer 501 is coupled to a set of digital-to-analog converter/amplifiers 504 and to a set of gain-controllable analog-to-digital converter/amplifiers 503. Digital-to-analog converter/amplifier set 504 is further coupled to transmitting transducer roller device 202, and gain-controllable analog-to-digital converter/amplifier set 503 is coupled to receiving transducer roller device 203. In addition, encoder/roller assembly sensor 407, auxiliary sensors 408 and 409, and sensor array 410 are coupled to computer 501.

In operation, computer 501 executes a stored program and provides digital ultrasonic pulse waves to digital-to-analog converter/amplifier set 504. Digital-to-analog converter/amplifier set 504 converts the digital ultrasonic pulse waves to high-power analog signals that are sent to transmitting transducers 204–208 (as shown in FIG. 2B), located in transmitting transducer roller device 202. The high-power analog signals drive transmitting transducers 204–208 to produce broadband ultrasonic pulses of predetermined phases and frequencies. In one embodiment, the broadband ultrasonic pulses preferably have a center frequency of approximately 180 kHz. It will be understood to those of ordinary skill in the art that other frequencies may also be used.

Transmitting transducers 204–208 transmit the broadband ultrasonic pulses through wooden member 201 and on to receiving transducers 209–213 (as discussed with reference to FIG. 2B). Receiving transducers 209–213 direct the received signals to gain-controllable analog-to-digital converter/amplifier set 503. Gain-controllable analog-to-digital converter/amplifier set 503 then provides the signals back to computer 501. Gain-controllable analog-to-digital converter/amplifier set 503 preferably provides at least eight bits of resolution and a sampling speed of at least two and one-half the center frequency of the ultrasonic wave being transmitted. Gain-controllable analog-to-digital converter/amplifier set 503 provides for amplification over a fifty decibel range as controlled by computer 501.

After receiving the signal from gain-controllable analog-to-digital converter/amplifier set 503, computer 501 collects and processes the received signals. The rate at which computer 501 signals digital-to-analog converter/amplifier set 504 to transmit the broadband pulses is determined by the desired spatial sampling rate and the speed of wooden member 201 as it moves along the z-axis in direction 302 (as shown in FIG. 3). Those skilled in the art will appreciate that the firing of the individual transmitters 204–208 must be sequenced so that there is no ambiguity in the received signals.

In addition to receiving and processing the ultrasonic waves, computer 501 receives inputs from encoder/roller assembly sensor 407, auxiliary sensors 408 and 409, and sensor array 410. These inputs provide useful information about the dimensions and positioning of wooden member 201, while single roller ultrasound device 225 provides information about the internal characteristics of wooden member 201.

Figure 6:
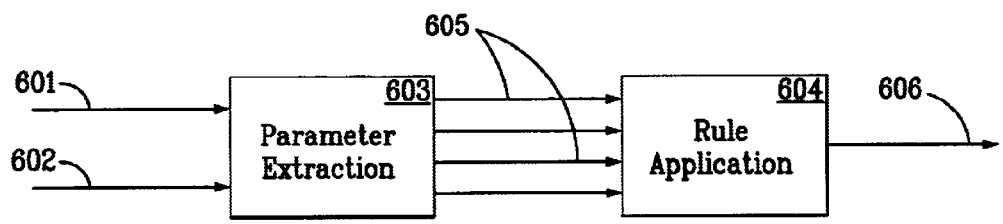
FIG. 6 is a block diagram of a processing program executed by a computer, according to the present invention.

FIG. 6 is a block diagram of a processing program executed by computer 501 for analyzing and detecting anomaly 214 by comparing a "standard" ultrasonic wave 601 to a received ultrasonic wave 602. Received ultrasonic wave 602 is an ultrasonic wave that has been passed through wooden member 201 (including an anomaly) and detected by receiving transducers 209–213. "Standard" ultrasonic wave 601 is created by passing a wave, derived from a digital version stored within computer 501, through a material without anomalies, such as clear wood or plastic, for example. By passing the wave through an "ideal" material, "standard" ultrasonic wave 601 provides a baseline measure, against which waves passed through wooden member 201 may be compared and analyzed.

Figure 7A:
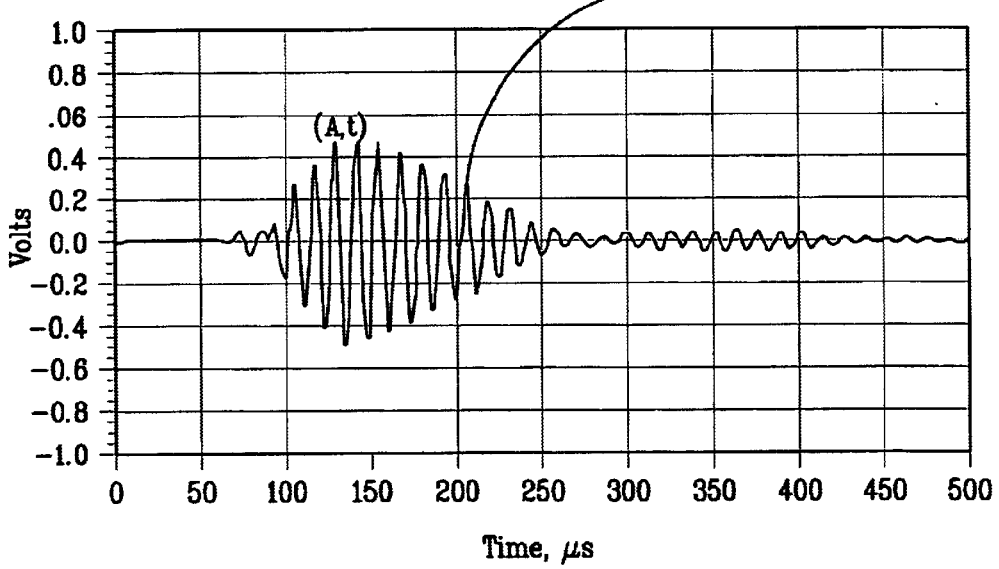
FIG. 7A is a graph of the voltage-signal strength over time for a "standard" ultrasonic wave.

FIG. 7A is a graph of "standard" ultrasonic wave 601, and FIG. 7B is a graph of received wave 602. FIGS. 7A and 7B show how the voltage-signal strength for each wave 601 and 602 varies over time. In particular, "standard" wave 601 has ordered pairs of amplitude values (A) having distinct times values (t), and received wave 602 similarly has a set of amplitude values (A=) at later time values (t=). While wave 601 has an amplitude of ±0.5 Volts and a generally triangular or Gaussian pulse shape, in contrast, wave 602 is of no more than ±0.1 Volts and has multiple, interfering waveforms within it. Thus, loss of energy and temporal coherence are effects of the passage of an ultrasonic wave through an anomaly.

Referring back to FIG. 6, "standard" wave 601 may be stored in computer 501 to facilitate comparison with the plurality of received waves 602 that are encountered as wooden member 201 is infiltrated with ultrasound waves. "Standard" wave 601 and received wave 602 are inputted to a parameter extraction device 603. Parameter extraction device 603 analyzes waves 601 and 602 and measures the various characteristics of each wave. Extracted parameters 605 may include any of a number of measurable and relevant characteristics of waves 601 and 602.

Further explanation of the processing of the parameters may be found in U.S. Pat. No. 6,029,522 to the present inventor, the contents of which are incorporated herein by reference. As described therein, other possible parameters include change in the total energy attenuation, change in spectral energy distribution, change in phase, and change in temporal energy distribution.

Once individual parameters 605 for waves 601 and 602 have been extracted, parameter extraction device 603 provides parameters 605 to rule application device 604. Rule application device 604 may be an empirically derived rule, developed by testing each of waves 601 and 602. For example, thresholds may be applied so that certain values of parameter 605 indicate a split while other thresholds of other parameters indicate a knot. The rule may be implemented by rules programmed into computer 501, or may be performed by artificial intelligence techniques such as neural networks or fuzzy logic, known to those in the art. Such rules consider each parameter 605 individually, or may combine two or more parameters 605.

FIG. 8 is a graph of two possible parameters 605. In particular, pulse length and insertion loss are plotted against distance along the z-axis. As shown in FIG. 8, peaks in pulse length 801 and troughs in insertion loss 802 correlate to regions 803 in which anomalies 214 are found in wooden element. Moreover, aside from simply identifying the existence of anomaly 214 the location of anomaly 803 may be determined, for example, to be a distance of sixteen inches along wooden member 201. Accordingly, as discussed with reference to FIG. 6, an empirically derived rule may be developed by testing each of pulse length 801 and 802 against a threshold, and logically ANDing the test results to produce an output indicating anomaly 214.

Referring back to FIG. 6, rule application device 604 then provides an output 606. Output 606 identifies anomalies 214, and further provides additional spatial location of anomalies 214 within wooden member 201.

Figure 9:
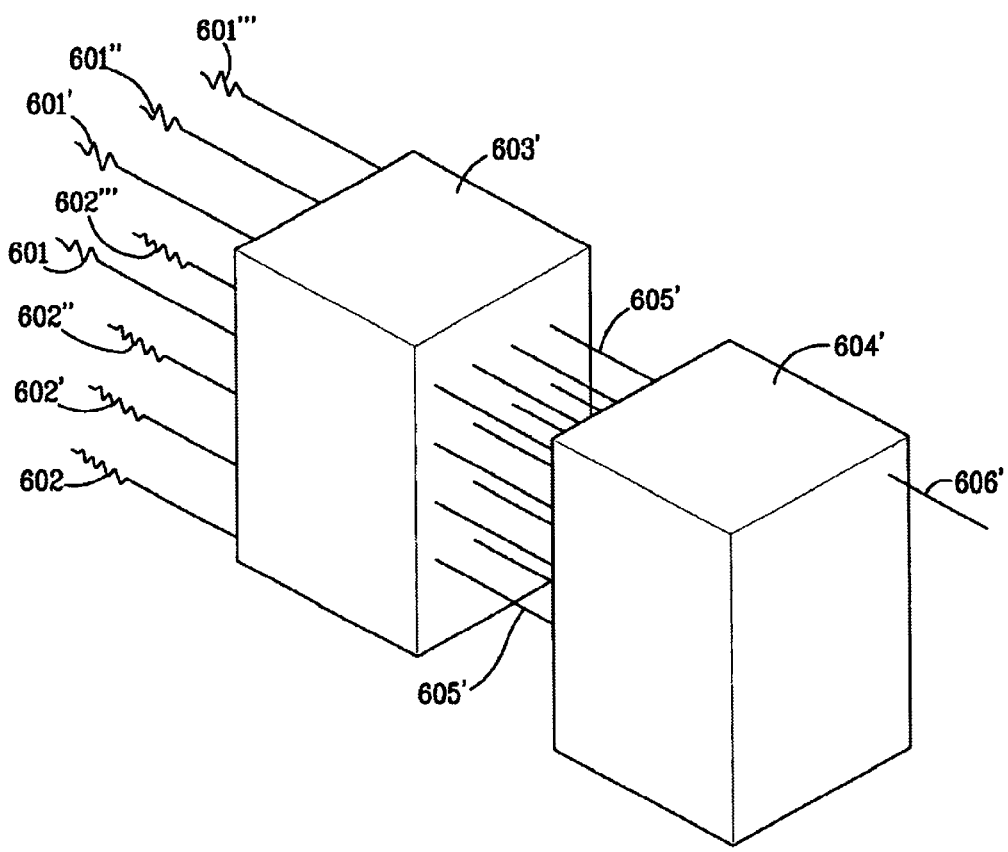
FIG. 9 is a block diagram showing a multi-parameter ultrasound measurement system, according to the present invention.

FIG. 9 is a block diagram showing a multi-parameter measurement applied to the x or z axis. Specifically, parameter extraction block 603 will receive a two-dimensional array of both "standard" waves 601–601'=> and received waves 602–602'=>. Parameters 605 of waves 601–601'=> and 602–602'=>, respectively, may be compared as described above with respect to FIG. 6. Also, cross-combinations of the waves 601–601'=> and 602–602'=> may be used to produce new parameters 605', for example spatial rates of change of parameters in the x or z direction. The parameters 605 and 605' may then be provided to rule application device 604, as discussed with reference to FIG. 6. Rule application device 604 may then provide an output 606 for determining the type, size and location of anomaly 214.

By measuring parameters 605–605' using a two-dimensional array of waves 601 and 602, additional information regarding anomaly 214 may be discovered, for example its location in the x-axis and/or y-axis. In particular, the x- and y-axis positions of anomaly 214 may be determined from the parameters derived from the location of individual transducer pair satisfying the rule of rule application device 604 in the same way that the z-axis position is determined as described with reference to FIG. 6. In this way, a map of the spatial location of anomalies 214 for wooden member 201 may be developed. Using this map, decisions may be made about length and location of cuts to wooden member 201 across the z-axis, in order to remove anomalies 214 from boards. These decisions may be augmented with decisions about rip cuts of wooden member 201 along the z-axis, so as to maximize the value of the cut wood.

In addition to its use during the cutting process, the present invention may be used to automate and optimize the cutting process. For example, after mapping all of the anomalies in wooden member 201, computer 501 may store an electronic map that identifies the locations of the identified anomalies in wooden member 201. Computer 501 may then be used to control a moveable saw, as understood in the art, to cut wooden member 201 so as to optimize its value. Alternatively, or in addition, computer 501 may be used to control a commercial sorting machine to mark or direct wooden member 201 in accordance with its strength or grade. Such proper grading and sorting allows more efficient use of lumber based on its determined strength, and also reduces the amount of lumber mistakenly discarded.

The present invention is directed to a system and method for detecting anomalies in a wooden member. However, it will be also understood that the detection method of the present invention may be combined with conventional visual or laser type knot and split detection equipment to augment those systems to obtain more robust detection or greater detection range.

The system disclosed has the following advantages over the prior art: 1) it reduces the mechanical complexity of the system; 2) it reduces the physical extent of the system in the direction of travel of the wooden member; thereby reducing cost and size of the system; 3) it provides enhanced analysis capability in terms of detecting features of the wooden member located between transducer elements; 4) it provides enhanced analysis capability in terms of generally enhanced resolution (twice the resolution per element location); 5) it provides enhanced analysis capability in terms of improved detection through redundancy of data elements.

While the present invention has been particularly shown and described with reference to the presently preferred embodiments thereof, it will be understood by those skilled in the art that the invention is not limited to the embodiments specifically disclosed herein. Those skilled in the art will appreciate that various changes and adaptations of the present invention may be made in the form and details of these embodiments without departing from the true spirit and scope of the invention as defined by the following claims.

What is claimed is:

1. An apparatus for detecting anomalies in a wooden member, where the wooden member is substantially planar, the apparatus comprising:
   a first roller device;
   a first array of transducers located within said first roller device, wherein each of said transducers in said first array are located in close proximity to each other along an axis;
   at least one acoustic isolator located between each of said transducers in said first array, wherein the acoustic isolator provides isolation between each of said transducers in said first array;
   a second roller device; and,
   a second array of transducers located within said second roller device, wherein a first transducer in said first array of transducers transmits an ultrasonic wave to more than one transducer in said second array of transducers, and wherein said first roller device and said second roller device are positioned such that said substantially planar wooden member may pass therebetween.

2. The apparatus of claim 1, wherein said first array of transducers and said second array of transducers maintain an orientation perpendicular to a direction of movement of said wooden member as said first roller device and said second roller device roll along said wooden member.

3. The apparatus of claim 1, wherein said first array of transducers and said second array of transducers operate in an ultrasonic frequency range.

4. The apparatus of claim 1, wherein said first array of transducers transmit ultrasonic waves through said wooden member that are received by said second array of transducers.

5. The apparatus of claim 1, wherein said first roller device rides along one side of said wooden member, and wherein said second roller device rides along another side of said wooden member.

6. The apparatus of claim 1, wherein each transducer in said first array of transducers is separated from another transducer by a distance equal to an acoustic insulator.

7. A system for detecting anomalies in a wooden member, where the wooden member is substantially planar, the system comprising:

a first roller device;

a first array of transducers located within said first roller device, wherein each of said transducers in said first array are located in close proximity to each other along an axis;

at least one acoustic isolator located between each of said transducers in said first array, wherein the acoustic isolator provides isolation between each of said transducers in said first array;

a second roller device;

a second array of transducers located within said second roller device, wherein a first transducer in said first array of transducers transmits an ultrasonic wave through said substantially planar wooden member that is received by more than one transducer in said second array of transducers; and a computer coupled to said first array of transducers and to said second array of transducers for mapping said anomalies in said substantially planar wooden member, wherein said computer receives a second ultrasonic wave from said second array of transducers.

8. The system of claim 7, wherein said computer provides a first ultrasonic wave of known characteristics to said first array of transducers, and wherein said computer compares a first ultrasonic wave of known characteristics to said second ultrasonic wave.

9. The system of claim 7, wherein said computer stores a standard ultrasonic wave, and wherein said computer compares said second ultrasonic wave with said standard ultrasonic wave.

10. The system of claim 9, wherein said standard ultrasonic wave is created by passing said first ultrasonic wave through a clear wood element or a plastic element.

11. The system of claim 7, wherein said computer provides a map of abnormalities within said wooden member.

12. The system of claim 7, further comprising at least one sensor coupled to said computer for identifying dimensions of said wooden member.

13. The system of claim 7, wherein said computer is in communication with a digital-to-analog converter/amplifier and with a gain-controllable analog-to-digital converter/amplifier.

14. The system of claim 13, wherein said gain-controllable analog-to-digital converter/amplifier provides at least eight bits of resolution for sampling said ultrasonic wave.

15. The system of claim 13, wherein said gain-controllable analog-to-digital converter/amplifier samples said ultrasonic wave at a rate of at least one-half a center frequency of said ultrasonic wave.

16. The system of claim 15, wherein said center frequency of said ultrasonic wave is 180 kilohertz.

17. The system of claim 7, further comprising at least one sensor coupled to said computer for identifying a positioning of said wooden member.

* * * * *

UNITED STATES PATENT AND TRADEMARK OFFICE
CERTIFICATE OF CORRECTION

PATENT NO. : 6,684,705 B1
DATED : February 3, 2004
INVENTOR(S) : Mark E. Schafer, Raymond W. McIntyre and Michael K. Knauer It is certified that error appears in the above-identified patent and that said Letters Patent is hereby corrected as shown below:

<u>Column 2,</u>
Line 51, delete "roil" and insert -- roll --.

Signed and Sealed this

Sixth Day of July, 2004

JON W. DUDAS
*Acting Director of the United States Patent and Trademark Office*